(12) United States Patent
Amiot et al.

(10) Patent No.: US 10,070,869 B2
(45) Date of Patent: Sep. 11, 2018

(54) BONE AND TOOL TRACKING WITH MEMS IN COMPUTER-ASSISTED SURGERY

(75) Inventors: Louis-Philippe Amiot, Hampstead (CA); Pierre Couture, Montréal (CA); Catherine Proulx, Verdun (CA); Trong Tin Nguyen, Laval (CA); Myriam Valin, Laval (CA)

(73) Assignee: ORTHOSOFT INC., Montreal (CA)

( * ) Notice: Subject to any disclaimer, the term of this patent is extended or adjusted under 35 U.S.C. 154(b) by 519 days.

(21) Appl. No.: 13/035,264

(22) Filed: Feb. 25, 2011

(65) Prior Publication Data
US 2012/0220859 A1    Aug. 30, 2012

(51) Int. Cl.
| | | |
|---|---|---|
| *A61B 5/06* | (2006.01) | |
| *A61B 17/15* | (2006.01) | |
| *A61B 17/00* | (2006.01) | |
| *A61B 34/20* | (2016.01) | |

(52) U.S. Cl.
CPC ............ *A61B 17/157* (2013.01); *A61B 34/20* (2016.02); *A61B 2017/00725* (2013.01); *A61B 2034/2048* (2016.02)

(58) Field of Classification Search
None
See application file for complete search history.

(56) References Cited

U.S. PATENT DOCUMENTS

| | | | |
|---|---|---|---|
| 2004/0152972 A1 | 8/2004 | Hunter | |
| 2009/0247863 A1* | 10/2009 | Proulx et al. | 600/426 |
| 2009/0248044 A1* | 10/2009 | Amiot et al. | 606/130 |
| 2011/0160572 A1* | 6/2011 | McIntosh et al. | 600/424 |
| 2014/0364858 A1* | 12/2014 | Li et al. | 606/91 |
| 2014/0375784 A1* | 12/2014 | Massetti | 348/74 |

FOREIGN PATENT DOCUMENTS

| | | |
|---|---|---|
| WO | 2006079211 A1 | 8/2006 |
| WO | WO2007085085 | 8/2007 |
| WO | 2009/117832 A1 | 10/2009 |
| WO | 2009/117833 A1 | 10/2009 |
| WO | WO2009117832 | 10/2009 |
| WO | WO2010111272 | 9/2010 |

OTHER PUBLICATIONS

U.S. Appl. No. 12/872,469, filed Aug. 31, 2010, by Pelletier et al.
U.S. Appl. No. 12/846,934, filed Jul. 30, 2010, by Amiot et al.

* cited by examiner

*Primary Examiner* — Jennifer Dieterle
(74) *Attorney, Agent, or Firm* — Norton Rose Fulbright Canada LLP

(57) ABSTRACT

A method tracks a tool with respect to a bone in computer-assisted surgery. A reference tracker with a MEMS unit is secured to the bone. The tracker outputs data relating to its orientation. A tool provided with a MEMS unit and secured to the bone is preset with an initial orientation. The tool outputs tracking data related to orientation of the tool once initialized. A trackable frame of reference relating the bone to the orientation of the tracker is created. The MEMS unit of the tool is initialized. A relation between the initial orientation of the tool and the orientation of the tracker at initialization of the MEMS unit of the tool is recorded. Orientational data of the tool relative to the frame of reference of the bone calculated using the relation is displayed. A computer-assisted surgery system for tracking a tool with respect to a bone after an initialization of a MEMS unit is also described.

15 Claims, 4 Drawing Sheets

BONE AND TOOL TRACKING WITH MEMS IN COMPUTER-ASSISTED SURGERY

FIELD OF THE APPLICATION

The present application relates to the calibration of tools for subsequently tracking the tools and operations performed with the tools with respect to body parts such as bones, using microelectromechanical sensors (MEMS) in computer-assisted orthopedic surgery.

BACKGROUND OF THE ART

One of the essential steps in navigating a bone and tools with MEMS sensors is to initially locate the bone relative to the sensors, i.e., creating a frame of reference or coordinate system. Some steps must be performed to create the frame of reference considering specifications of MEMS sensor systems. Specifications of MEMS sensor systems may include orientation tracking along two degrees of freedom only, or the absence of positional tracking. The steps comprise various manipulations of a sensor and/or bone, for the orientational setting of the sensor (hereinafter, the reference tracker) with respect to the bone. Once the orientational setting is completed, navigation steps may be performed, with the bone being tracked via the frame of reference using the reference tracker.

In some instances, the sensor must be constrained with respect to a bone for subsequent tracking. For femur tracking for example, the orientation of the sensor relative to the lateral axis can be constrained mechanically (e.g., with claws inserted under the posterior condyles) so that the sensor lateral axis is aligned with the lateral axis of the bone.

In other instances, various tools used to perform alterations on a bone must be calibrated with respect to a MEMS reference tracker, to be tracked during navigation. One example is the cutting block (a.k.a., positioning block), which may be mechanically constrained to the MEMS reference tracker for the calibration to be made. In such a case, specific manipulations must be executed by the operator to ensure that the positioning block is connected to the reference tracker for the calibration of the positioning block, for subsequent tracking and bone alterations.

SUMMARY OF THE APPLICATION

It is therefore an aim of the present disclosure to provide a novel method and system for tracking bones and tools using MEMS in computer-assisted surgery.

Therefore, in accordance with the present application, there is provided a method for tracking a tool with respect to a bone in computer-assisted surgery, comprising: securing a reference tracker with a MEMS unit to the bone, the reference tracker outputting tracking data relating to an orientation of the reference tracker; providing a tool with a MEMS unit, the tool being preset with an initial orientation and outputting tracking data related to an orientation of the tool once initialized; securing the tool to the bone; creating a trackable frame of reference relating the bone to the orientation of the reference tracker; initializing the MEMS unit of the tool; recording a relation between the initial orientation of the tool and the orientation of the reference tracker at initialization of the MEMS unit of the tool; and displaying orientational data of the tool relative to the frame of reference of the bone calculated using the relation.

Further in accordance with the present application, there is provided a computer-assisted surgery system for tracking a tool with respect to a bone, comprising: a reference tracker with a MEMS unit for outputting tracking data relating to an orientation of the reference tracker, the reference tracker being adapted to be secured to the bone; a tool with a MEMS unit preset with an initial orientation for outputting tracking data relating to an orientation of the tool once initialized, the tool being adapted to be secured to the bone; a CAS processing unit comprising an orientation setting unit for creating a trackable frame of reference relating the bone to the orientation of the reference tracker, a tool calibrator for recording a relation between the initial orientation of the tool and the orientation of the reference tracker at initialization, a tracking processor for calculating orientational data of the tool in the frame of reference of the bone using the relation from the tracking data, and an interface for displaying the orientational data.

DESCRIPTION OF THE EXEMPLARY EMBODIMENTS

Figure 1:
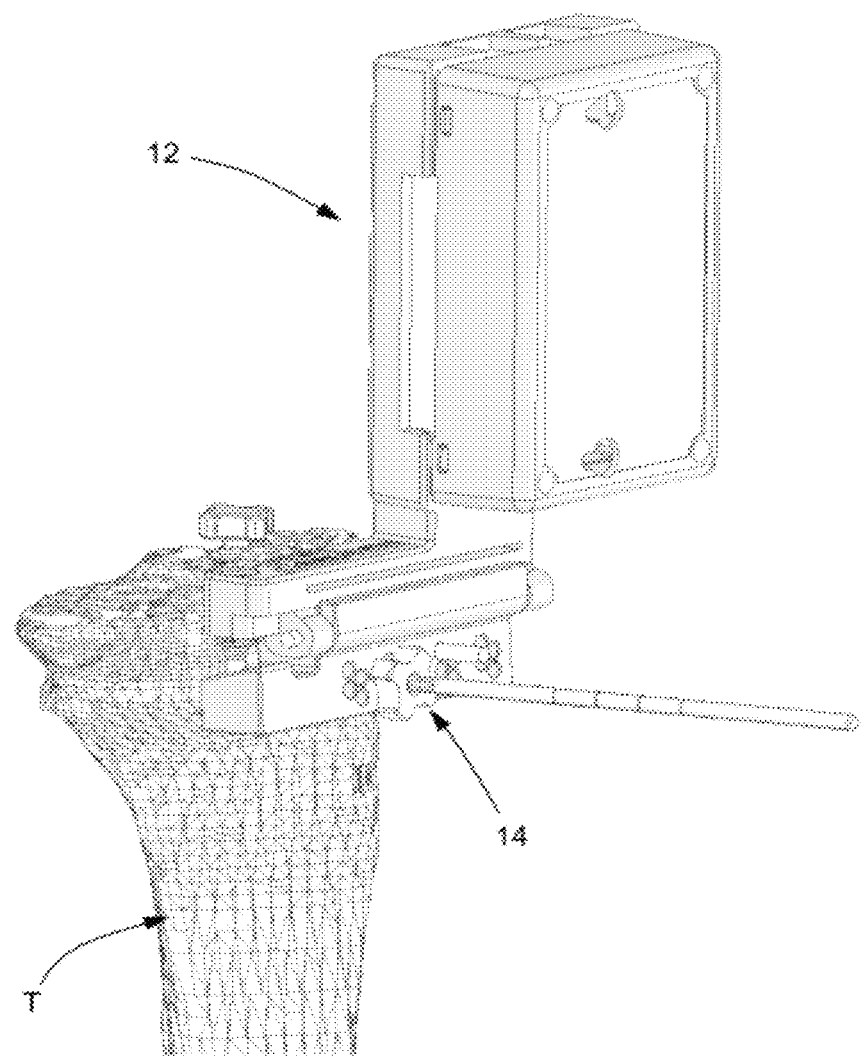
FIG. 1 is a perspective view of a cutting block as secured to a tibia.
Figure 2:
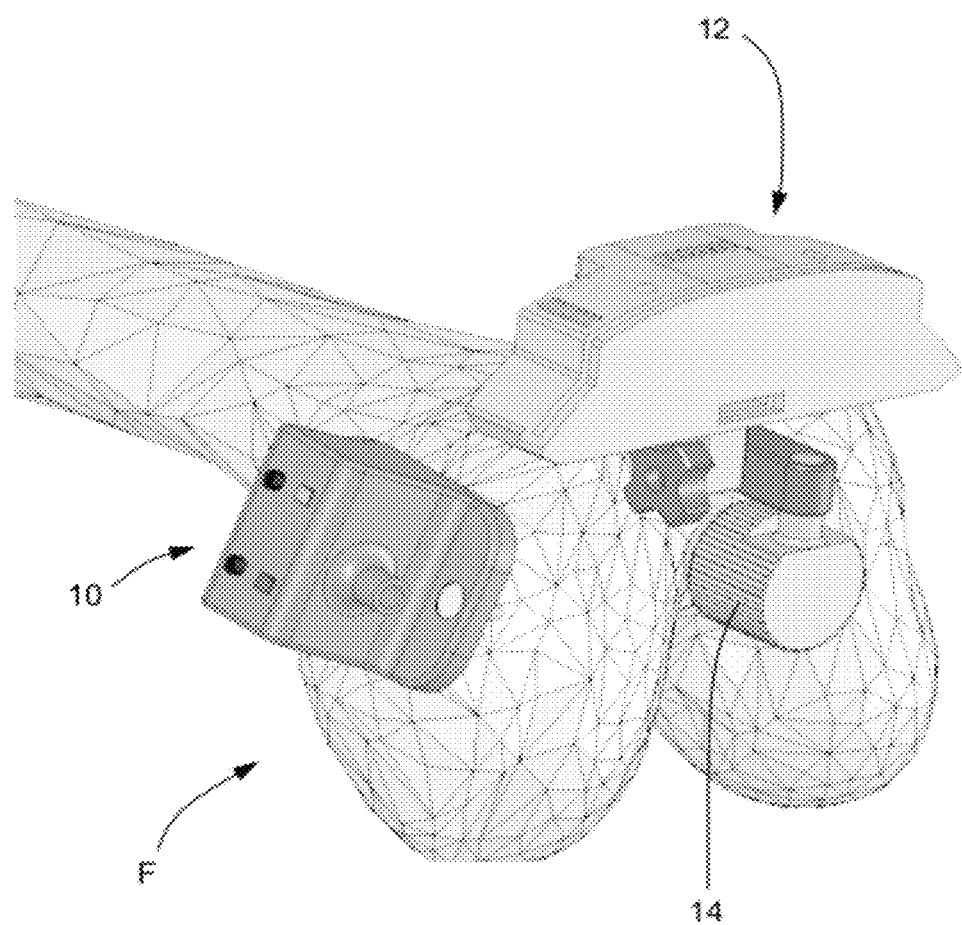
FIG. 2 is a perspective view of a reference tracker and cutting block secured to a femur.

Referring to the drawings and more particularly to FIGS. 1 and 2, a tibia T and a femur F are respectively illustrated with a reference tracker 10 (FIG. 2), and with a cutting block 12 (a.k.a., positioning block). The reference tracker 10 and the cutting block 12 are provided with micro-electromechanical sensors (MEMS) that provide readings pertaining to at least two degrees of freedom (DOFs) in rotation, although the MEMS could provide readings for more degrees of freedom, in rotation and/or translation, if appropriately equipped. The MEMS may comprise a gyroscope and/or accelerometer, or sets thereof, among other possibilities.

In FIG. 1, the cutting block 12 is secured to the tibia T adjacent to the tibial plateau at a top end of the tibia T, to serve as a guide for the cutting of planes, for the installation of an implant on the resulting resected tibia. An orientation adjustment mechanism 14 separates the anchor points of the cutting block 12 from the slot or slots serving as guides. Therefore, the MEMS are on the portion of the cutting block 12 integral with the slots, and consequently move therewith. Although not shown, a reference tracker 10 is also secured to the tibia T, and could be on the portion of the cutting block 12 anchored to the bone. The reference tracker 10 may also be physically separated from the cutting block 12.

In FIG. 2, the cutting block 12 is secured to the femur F adjacent to the knee end thereof, also to serve as a guide for the cutting of planes. The planes are then used as interface for an implant. In a fashion similar to the tibial application, the orientation adjustment mechanism 14 separates the anchor points of the cutting block 12 from the slots serving as guides. Therefore, the MEMS are on the portion of the cutting block 12 integral with the slots, and consequently move therewith. The reference tracker 10 is also secured to the tibia T, and is physically separated from the cutting block 12 in FIG. 2. The reference tracker 10 could also be on the portion of the cutting block 12 anchored to the bone.

Figure 4:
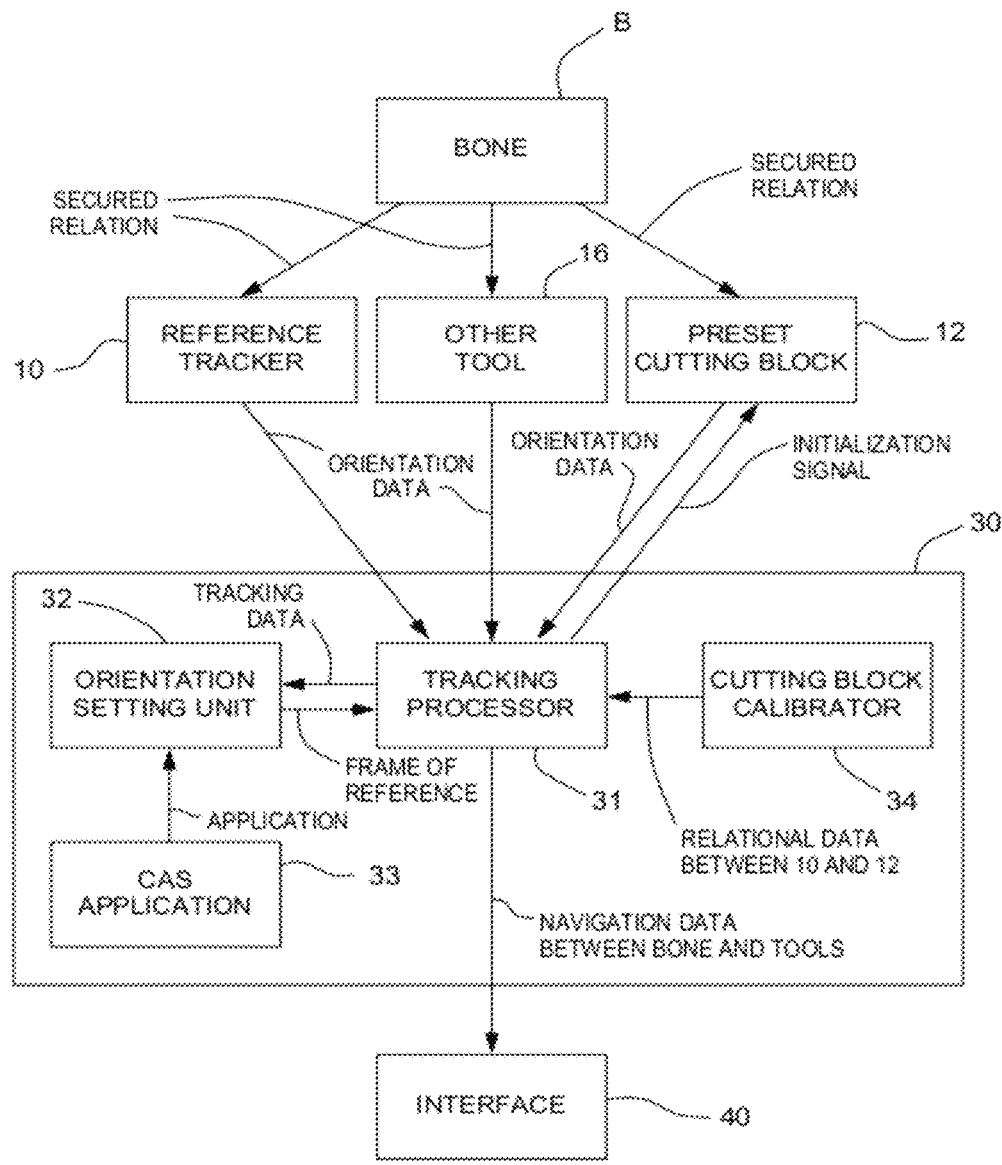
FIG. 4 is a block diagram of a system for tracking a bone and tools in computer-assisted surgery in accordance with the present disclosure.

As shown in FIG. 4, another tool or other tracker 16 (i.e., digitizing tools) may be used in the process of digitizing a frame of reference for the bone, as will be described hereinafter. According to one embodiment, the tool 16 is a tibial digitizer as described in U.S. patent application Ser. No. 12/872,469, filed on Aug. 31, 2010, incorporated herein by reference.

Figure 3:
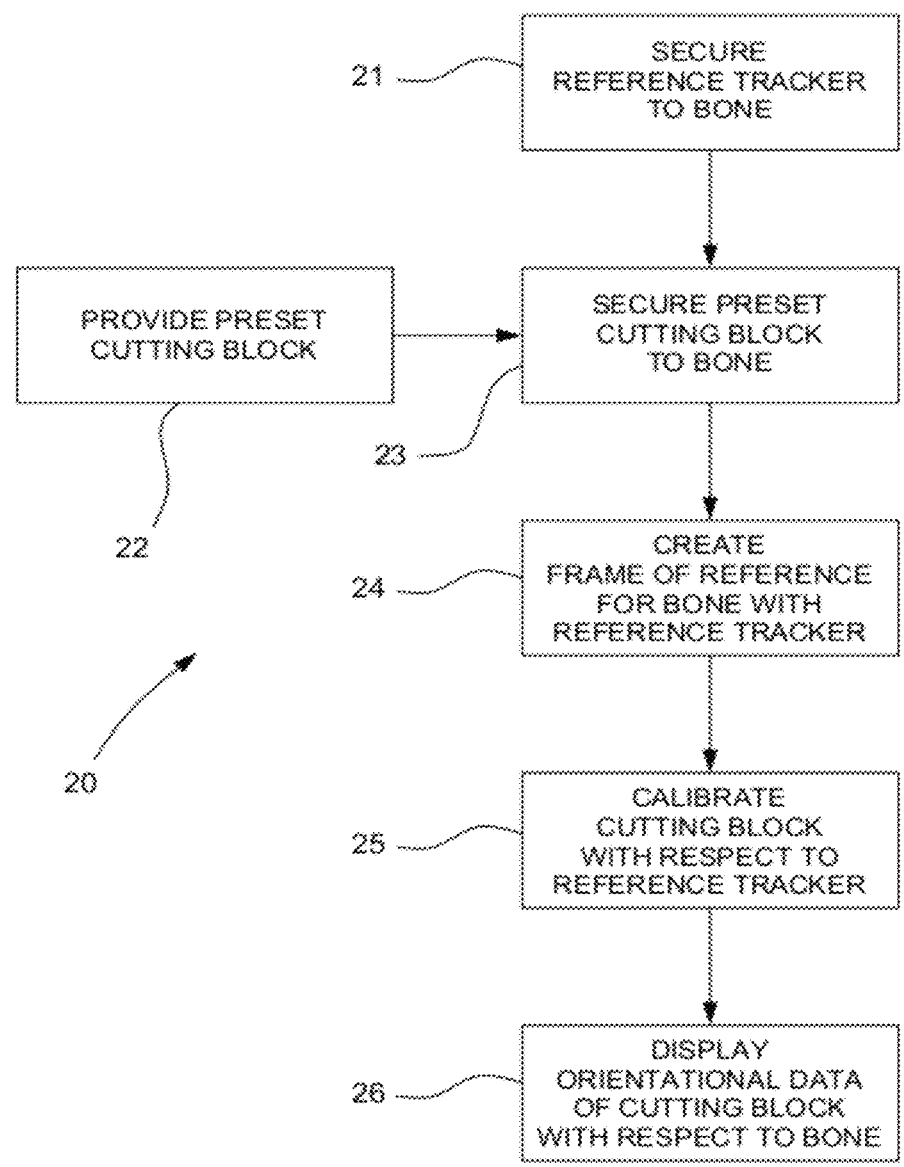
FIG. 3 is a flowchart of a method for tracking a bone and tools in computer-assisted surgery in accordance with an embodiment of the present disclosure.

Referring to FIG. 3, a method 20 is illustrated for the calibration of the cutting tool 12 or any other tool with respect to a bone for subsequent surgical steps to be performed on the bone.

According to 21, a reference tracker such as the reference tracker 10 is secured to the bone. The reference tracker provides tracking data pertaining to at least two degrees of orientation. The reference tracker 10 may be secured in a specific orientation with respect to a bone. For instance, a two-DOF reference tracker 10 can be constrained mechanically (e.g., with claws inserted in the bone) so that the sensor lateral axis is aligned with the lateral axis of the tibia T, in the case of a tibial application.

Other factors influencing the securing of the reference tracker 10 to the bone include the number of DOFs tracked by the reference tracker 10, the incision of soft tissue and resulting exposed bone, the parts of the bone exposed (e.g., thicker parts).

According to 22, a cutting block 12 is provided, for the surgical steps to be subsequently performed on the bone using the cutting block 12. The cutting block 12 is preset, in that the orientation of the tracking axes of the MEMS of the cutting block is known when the cutting block 12 is initialized. In one embodiment, the cutting block 12 tracks two DOFs in orientation, and the axes are orthogonal to the cutting block 12 at initialization.

According to 23, the preset cutting block 12 is secured to the bone, without yet being initialized. In the tibial application, and in the femoral application, the cutting block 12 tracks two DOFs, and is installed in close proximity to the knee end of the bone. The cutting block 12 is used to cut a transverse plane. In an embodiment, the cutting block 12 could also be used to cut anterior/posterior planes. Therefore, the orientation adjustment mechanism 14 will allow the cutting block 12 to be rotated about the lateral axis and the anterior/posterior axis of the bone.

According to 24, a frame of reference is created and set for the bone with respect to the reference tracker 10. The frame of reference may include at least one axis of the bone, and in some instances a three-axis coordinate system. In the tibial application, the frame of reference comprises a longitudinal axis, such as the mechanical axis of the tibia, while the mechanical axis of the femur may be defined for the frame of reference in the femoral application. The coordinate systems may also comprise an anterior-posterior axis for the tibia, and a medio-lateral axis for the femur.

Various methods have been developed and described to create frames of reference using MEMS reference trackers 10 for tracking of bones, for the subsequent tracking of the bones. A method is described in United States Patent Application Publication No. 2009/0247863, published on Oct. 1, 2009, incorporated herein by reference. Another method is described in United States Patent Application Publication No. 2009/0248044, published on Oct. 1, 2009, incorporated herein by reference. Yet another method is described, for a femoral application, in U.S. patent application Ser. No. 12/846,934, filed on Jul. 30, 2010, also incorporated herein by reference. Of interest in these references are the methods and systems to create a frame of reference (e.g., a coordinate system) with a MEMS sensor unit (i.e., reference tracker) with respect to a bone for the subsequent tracking of the bone in orientation.

The other tool 16 may be used to define an axis of the bone. For instance, a tibial digitizer is described in U.S. patent application Ser. No. 12/872,469, incorporated herein by reference. The tibial digitizer is used to identify the orientation of the mechanical axis of the tibia T. The tibial digitizer may also be used to identify the anterior-posterior axis for the tibia T.

According to 25, with the bone now being tracked in orientation using the reference tracker 10, the preset cutting block 12 is calibrated with respect to the frame of reference (e.g., coordinate system) resulting from 24. When the MEMS unit of the cutting block 12 is ready to be initialized, the cutting block 12 has been secured to the bone, and the bone is being tracked in orientation using the reference tracker 10. Therefore, at the moment at which the MEMS unit on the preset cutting block 12 is initialized, the relation is recorded between the preset axes of the MEMS unit on the cutting block 12 and the axes of the frame of reference of the bone tracked via the reference tracker 10. The relation between the reference tracker 10 and the cutting block 12 is therefore known, and related to the frame of reference of the bone, as tracked by the reference tracker 10. Appropriate movements of the tibia T are performed to gather tracking data that will be used to establish the relational data between the reference tracker 10 and the cutting block 12. In an embodiment, the tibia T is moved in an adduction/abduction motion. In another embodiment, the tibia is moved in flexion/extension.

Alternatively, the preset cutting block 12 may be initialized prior to the creation of the frame of reference of the bone in 24. The preset cutting block 12 may be initialized to record its relation to the reference tracker 10. In this case, at the moment at which the MEMS unit on the preset cutting block 12 is initialized, the relation is recorded between the preset axes of the MEMS unit on the cutting block 12 and the instant orientation of the axes of the reference tracker 10, for subsequent calculation of the orientational data relating the cutting block 12 to the frame of reference of the bone. Again, appropriate movements of the tibia T are performed to gather tracking data that will be used to establish the relational data between the reference tracker 10 and the cutting block 12.

It is pointed out that the aforedescribed method may be performed on bone models or cadavers. The sequence of steps of the method may also be in any other suitable order, as explained above for the initialization of the preset cutting block 12 with respect to the reference tracker 12, as opposed to the frame of reference of 24. As another example, the cutting block 12 may be secured to the bone after the frame of reference has been defined.

In one embodiment, the MEMS unit of the cutting block 12 is a "zero" initial orientation for each rotational axis it tracks. In the "zero" initial orientation, the rotational axes are orthogonal to the MEMS unit of the cutting block 12. Other initial configurations are possible as well.

Some applications (e.g., femoral application) may require other steps to be performed to calibrate the cutting block 12 relative to the reference tracker 10. In the femoral application, similarly to the tibial application, additional movements of calibration are performed before or after the creation of the frame of reference of the tibia to define the relation between all axes of the cutting block 12 and that of the reference tracker 12. The additional movements may, for example, include placing the femur in an orientation of extreme internal rotation, and another of extreme external rotation, to record additional information.

According to 26, with the cutting block 12 being calibrated, orientational data is calculated and displayed using the relation between the cutting block 12 and the reference tracker 12. As an example, the orientation of the cutting block 12 may be tracked with reference to the frame of reference of the bone. Therefore, the orientation adjustment mechanism 14 is used to adjust the orientation of the slot or slots of the cutting block 12. The data related to the relative orientations between bone and slots of the cutting block 12 may be displayed in a separate user interface, or directly on the cutting block 12. For instance, the cutting block 12 may be provided with light displays indicating that a desired orientation has been reached. When the mechanical axis of the bone is normal or parallel to the plane of a slot of the cutting block 12, an indication signal (e.g., visual, audible) is emitted to the operator.

Referring to FIG. 4, a CAS unit for tracking bones and tools, such as the reference tracker 10, the cutting block 12 and other tools 16 is generally shown at 30. The trackers 10, 16 and the cutting block 12 form, with the CAS unit 30 and with interfaces, a CAS system.

The CAS unit 30 has a tracking processor 31 that receives the orientation data from the MEMS on the trackers 10, 16 and the cutting block 12, for the tracking of the trackers 10, 16 and of the cutting block 12. With additional data provided by other components of the CAS unit 30, the tracking processor calculates orientational data relating the cutting block 12 to a frame of reference defined for the bone using the tracking data of the reference tracker 10. The tracking processor 31 may also initialize the preset cutting block 12, by way of an initialization signal.

The orientation setting unit 32 receives the tracking data for the various trackers and tools used with the CAS unit 30. According to an application 33 that is operated by the orientation setting unit 32, a frame of reference (e.g., a coordinate system) is set for the bone B, using the tracker 10, and any other required tracker such as the tool 16. The application 33 may provide guiding data, to be displayed during the various steps to guide the operator in performing the appropriate sequence of manipulations.

According to an embodiment, the CAS application 33 corresponds to any one of the aforementioned tibial and femoral applications, whereby the orientation setting unit 32 defines the axis or axes of the frame of reference of the bone B using any one of the methods described above. As a result of the orientation setting unit 32, the tracking processor 31 produces tracking data for the bone B from the orientation data of the reference tracker 10, which tracking data may be displayed using an interface 40.

A cutting block calibrator 34 (i.e., a tool calibrator 34) is provided to initialize the preset cutting block 12, and to record a relation between the orientations of the preset cutting block 12 and of the reference tracker 10 or of the frame of reference of the bone B. As a result of the cutting block calibrator 34, the tracking processor 31 produces orientational data relating the tracked cutting block 12 to the frame of reference of the bone, which orientational data may be displayed using the interface 40, using the recorded relation between the cutting block 12 and the reference tracker 10, at the initialization.

The interface 40 may be part of the CAS unit 30, although shown as being separate therefrom. Due to the miniaturization of CAS tools, the interface 40 may be integrated directly on the tools, for instance in the form of lights (LEDs) or the like. In one particular embodiment, the lights are in a scale format, indicating when a suitable orientation is reached.

The invention claimed is:

1. A method for tracking a tool with respect to a bone in computer-assisted surgery for subsequently performing alterations to the bone with the tool, comprising:
    securing a reference tracker with a MEMS unit to the bone, the reference tracker outputting tracking data relating to an orientation of the reference tracker;
    securing a tool with a guiding feature and a MEMS unit to the bone, the guiding feature configured for guiding alterations to a bone and movable relative to the bone when the tool is secured to the bone, and the MEMS unit of the tool being virtually preset with an initial orientation associated to the guiding feature of the tool and outputting tracking data related to an orientation of the tool once initialized, the initial orientation being axes of the MEMS in said tracking data, the axes being representative of a preset virtual alignment of the MEMS unit as secured to the tool;
    creating a trackable frame of reference relating the bone to the orientation of the reference tracker;
    initializing the MEMS unit of the tool whereby the MEMS unit of the tool produces said tracking data;
    recording a relation between the initial orientation of the tool and the orientation of the reference tracker at initialization of the MEMS unit of the tool, using said tracking data from the MEMS unit of the reference tracker and the MEMS unit of the tool;
    after recording said relation, performing bone alterations using the tool and using a display of orientational data of the guiding feature of the tool relative to the frame of reference of the bone calculated using the relation to reach a desired orientation of the guiding feature of the tool through movements of the guiding feature of the tool relative to the bone; and
    wherein securing the reference tracker and the tool to the bone comprises securing the reference tracker and the tool to a bone at separate locations.

2. The method according to claim 1, wherein securing the tool comprises securing a cutting block, in which the guiding feature is at least one cutting slot, to the bone by an orientation adjustment mechanism allowing the adjustment of the orientation of the cutting block, and wherein using a display of orientational data comprises using a display of data pertaining to an orientation of the at least one cutting slot in the cutting block relative to the frame of reference of the bone.

3. The method according to claim 2, wherein securing the reference tracker and the cutting block to the bone comprises securing the reference tracker and the cutting block to a tibia.

4. The method according to claim 3, wherein creating the trackable frame of reference comprises determining at least a mechanical axis of the tibia.

5. The method according to claim 2, wherein securing the reference tracker and the cutting block to the bone comprises securing the reference tracker and the cutting block to a femur.

6. The method according to claim 5, wherein creating the trackable frame of reference comprises determining at least a mechanical axis of the femur.

7. The method according to claim 1, wherein creating a trackable frame of reference comprises creating a coordinate system of three axes.

8. The method according to claim 1, wherein securing the tool preset with the initial orientation comprises securing the tool with axes being orthogonal to the MEMS unit on the tool.

9. The method according to claim 1, wherein the method is performed on a bone model or a cadaver.

10. A computer-assisted surgery system for tracking a tool with respect to a bone for assisting in subsequently performing alterations to the bone with the tool, comprising:
   a reference tracker with a MEMS unit for outputting tracking data relating to an orientation of the reference tracker, the reference tracker being adapted to be secured to the bone;
   a tool with a guiding feature configured for guiding alterations to a bone, and a MEMS unit virtually preset with an initial orientation associated to the guiding feature of the tool for outputting tracking data relating to an orientation of the guiding feature of the tool once initialized, the tool being adapted to be secured to the bone with the guiding feature movable relative to the bone, the initial orientation being axes of the MEMS in said tracking data, the axes being representative of a virtual preset alignment of the MEMS unit and the tool;
   a CAS processing unit comprising:
      an orientation setting unit for creating a trackable frame of reference relating the bone to the orientation of the reference tracker;
      a tool calibrator for recording a relation between the initial orientation of the tool and the orientation of the reference tracker at initialization by receiving the tracking data from the MEMS unit of the tool and of the reference tracker;
      a tracking processor for calculating orientational data of the guiding feature of the tool in the frame of reference of the bone through movements of the guiding feature of the tool relative to the bone using the relation and the tracking data from the MEMS unit of the tool and of the reference tracker, the calculating occurring after the recording of said relation and during alterations to the bone using the guiding feature of the tool; and
      an interface for displaying the orientational data;
   wherein the reference tracker and the tool are secured to the bone at separate locations.

11. The computer-assisted surgery system according to claim 10, wherein the tool is a cutting block connected to the bone with an orientation adjustment mechanism, wherein the guiding feature is at least one cutting slot and wherein the orientational data comprises an orientation of at least one cutting plane of the at least one cutting slot relative to the frame of reference of the bone.

12. The computer-assisted surgery system according to claim 10, wherein the frame of reference comprises at least a mechanical axis of the bone.

13. The computer-assisted surgery system according to claim 10, the initial orientation of the guiding feature of the tool comprises axes being orthogonal to the MEMS unit on the tool.

14. The computer-assisted surgery system according to claim 10, wherein the tool secured to the bone has an orientation adjustment mechanism supporting the guiding feature and the MEMS unit, the orientation adjustment mechanism providing two degrees of freedom of orientation to the MEMS unit relative to the bone, and wherein the preset virtual alignment of the MEMS unit has the axes in known alignment with the two degrees of freedom of orientation.

15. The method according to claim 1, wherein securing the tool comprises securing the tool with an orientation adjustment mechanism supporting the guiding feature and the MEMS unit, the orientation adjustment mechanism providing two degrees of freedom of orientation to the MEMS unit relative to the bone, and wherein the preset virtual alignment of the MEMS unit has the axes in known alignment with the two degrees of freedom of orientation.

* * * * *